US009316619B2

(12) United States Patent
Lombardo et al.

(10) Patent No.: US 9,316,619 B2
(45) Date of Patent: Apr. 19, 2016

(54) NON DESTRUCTIVE EVALUATION SCANNING PROBE WITH SELF-CONTAINED MULTI-AXIS POSITION ENCODER

(71) Applicants: Erik A. Lombardo, Sharon, SC (US); David S. Segletes, York, SC (US); Timor Abu-Jaber, Charlotte, NC (US)

(72) Inventors: Erik A. Lombardo, Sharon, SC (US); David S. Segletes, York, SC (US); Timor Abu-Jaber, Charlotte, NC (US)

(73) Assignee: Siemens Energy, Inc., Orlando, FL (US)

( * ) Notice: Subject to any disclaimer, the term of this patent is extended or adjusted under 35 U.S.C. 154(b) by 352 days.

(21) Appl. No.: 13/956,453

(22) Filed: Aug. 1, 2013

(65) Prior Publication Data
US 2015/0035523 A1 Feb. 5, 2015

(51) Int. Cl.
| G01N 27/82 | (2006.01) |
| G01N 27/90 | (2006.01) |
| G01N 29/04 | (2006.01) |
| G01N 29/34 | (2006.01) |
| G01N 29/44 | (2006.01) |
| G01N 29/22 | (2006.01) |
| G01N 29/265 | (2006.01) |
| G01N 29/27 | (2006.01) |

(52) U.S. Cl.
CPC ............ *G01N 27/902* (2013.01); *G01N 27/908* (2013.01); *G01N 27/9013* (2013.01); *G01N 29/04* (2013.01); *G01N 29/225* (2013.01); *G01N 29/226* (2013.01); *G01N 29/265* (2013.01); *G01N 29/27* (2013.01); *G01N 29/34* (2013.01); *G01N 29/44* (2013.01)

(58) Field of Classification Search
CPC . G01N 27/902; G01N 27/908; G01N 29/265; G01N 29/04–29/043; G01N 29/34–29/345
USPC .................................................. 324/228–243
See application file for complete search history.

(56) References Cited

U.S. PATENT DOCUMENTS

| 3,955,405 | A  | * | 5/1976  | Couture   | ............ | G01N 29/0627 340/659 |
| 8,087,298 | B1 | * | 1/2012  | DiMambro  | .......... | G01N 29/226 73/629 |
| 8,983,794 | B1 | * | 3/2015  | Motzer    | .................... | G01C 9/00 702/150 |
| 2005/0015209 | A1 | * | 1/2005 | Wuebker  | .............. | G01N 27/902 702/38 |
| 2009/0316531 | A1 | * | 12/2009 | Brignac | ............. | G01N 29/2462 367/178 |
| 2011/0087443 | A1 | * | 4/2011 | Zhang    | ................ | G01N 29/0654 702/39 |
| 2011/0257903 | A1 |   | 10/2011 | Imbert et al. | | |
| 2014/0083192 | A1 | * | 3/2014 | Oberdoerfer | ....... | G01S 7/52061 73/618 |
| 2014/0183341 | A1 | * | 7/2014 | Glass, III | ............. | G01N 29/265 250/215 |
| 2014/0278221 | A1 | * | 9/2014 | Troy    | ...................... | G01C 22/02 702/151 |
| 2015/0122055 | A1 | * | 5/2015 | Puckett | .................. | G01S 17/66 73/865.8 |

FOREIGN PATENT DOCUMENTS

| JP | 2006170766 A | 6/2006 |
| WO | 2007021541 A2 | 2/2007 |

* cited by examiner

*Primary Examiner* — Patrick Assouad
*Assistant Examiner* — Demetrius Pretlow (57) ABSTRACT

A scanning probe for an industrial nondestructive evaluation (NDE) ultrasound or eddy current scanning system. The scanning probe gathers reflected waveform data indicative of internal characteristics of the test object. The scanning probe also includes a self-contained multi-axis position encoder that correlates both multi-dimensional probe underside translation and rotation motion across the test sample surface with the multi-dimensional spatial location on the test object surface. The position encoder compensates for probe rotation that would otherwise negatively impact probe position determination accuracy. A data acquisition system combines sets of positional and waveform data for processing by an NDE analyzer.

17 Claims, 6 Drawing Sheets

NON DESTRUCTIVE EVALUATION SCANNING PROBE WITH SELF-CONTAINED MULTI-AXIS POSITION ENCODER

BACKGROUND OF THE INVENTION

1. Field of the Invention

The invention relates to nondestructive evaluation of non-living test samples, also referred to as industrial NDE, by reflected waveform scanning: for example ultrasound or eddy current NDE scanning. The scanning probe includes a self-contained multi-axis position encoder that correlates both multi-dimensional probe underside translation and rotation motion across the test sample surface with the multi-dimensional spatial location on the test object surface. The position encoder compensates for probe rotation that would otherwise negatively impact probe position determination accuracy.

2. Description of the Prior Art

Ultrasound and eddy current industrial NDE scanners transmit penetrating waveforms into an inanimate test object sample and capture the reflected waveform. The reflective waveform data are analyzed to extract information about internal characteristics of the test object, including by way of nonlimiting example sample thickness and other internal dimensions, internal non-homogeneities, such as cracks or voids and density variations.

NDE of an industrial object by an eddy current modality identifies discontinuities, such as cracks or voids, by passage of a steady state alternating current or pulsed current waveform in a test probe transmitter coil that is electromagnetically coupled in close proximity to an electrically conductive test object. The changing current flow in the probe transmitter generates a changing transmitted magnetic field waveform that in turn induces a generated eddy current in the electromagnetically coupled test object. Variations in the phase and magnitude of these generated eddy currents within the test object create a responsive or reflected magnetic field waveform that is in turn sensed by a test probe receiver coil as an induced received or reflected current flow. In some known eddy current NDE systems the test probe's transmitter coil also functions as the receiver coil. Thus, variations in the electrical conductivity or magnetic permeability of the test object, or the presence of any flaws, will cause a change in eddy current and a corresponding change in the phase and amplitude of the reflected magnetic waveform as sensed by the test probe receiver changes in its current waveform. Amplitude and intensity of an eddy current within a test object will stay substantially constant if its magnetic transmission characteristics (which impact the reflected waveform) are substantially constant. However, anomalies in the test object alter its magnetic transmission characteristics at the anomaly location. Accordingly, anomalies and their spatial location within the test object can be detected by determining if the magnetic transmission characteristics of the material being scanned are consistent with the presence or absence of an anomaly at each scan spatial location.

NDE of an industrial object by an ultrasonic modality identifies discontinuities, such as cracks or voids, by transmission of pulsed sound waves through the object and reception of reflected "echo" waveforms. Often pulse transmission and echo reception are performed by a probe device. The reflected waveform is analyzed for acoustic patterns that are correlated with discontinuities in the inspected test object sample. A discontinuity present in a given material will reflect a different waveform than discontinuity-free homogeneous material. Generally, relative distance between the ultrasonic probe and the discontinuity is a function of elapsed time between probe transmission of the sound wave and reception of the reflected waveform. Discontinuity physical size (i.e., its occupied volume) is indirectly correlated with the echo waveform energy (e.g., amplitude), because reflected energy is impacted by a multitude of physical factors including discontinuity physical size and dimensions, as well as attenuation of the wave energy as it travels through the inspected material.

Reflected or "echo" wave amplitude alone from a single waveform scan orientation may not provide sufficient information to determine the estimated envelope of physical dimensions and profile of a discontinuity. Dimensional and profile information is useful for making an ultimate inspection determination whether the inspected part is acceptable to use in industrial service. In the past, analysis of a plurality reflected waveforms taken from different respective probe scan positions about the inspected object and variation of transmitted wave frequency/wavelength has enabled inspectors to construct composite spectral and/or visual images of a scanned object that correlate the approximate discontinuity size with that of a known hole size or a plurality of adjoining holes. Depending upon the physical dimensions of the scanned inanimate object and the relative dimensions of discontinuities, ultrasonic images have been constructed of sufficient resolution evaluate potential impact on the inspected part's future use in service.

Figure 1:
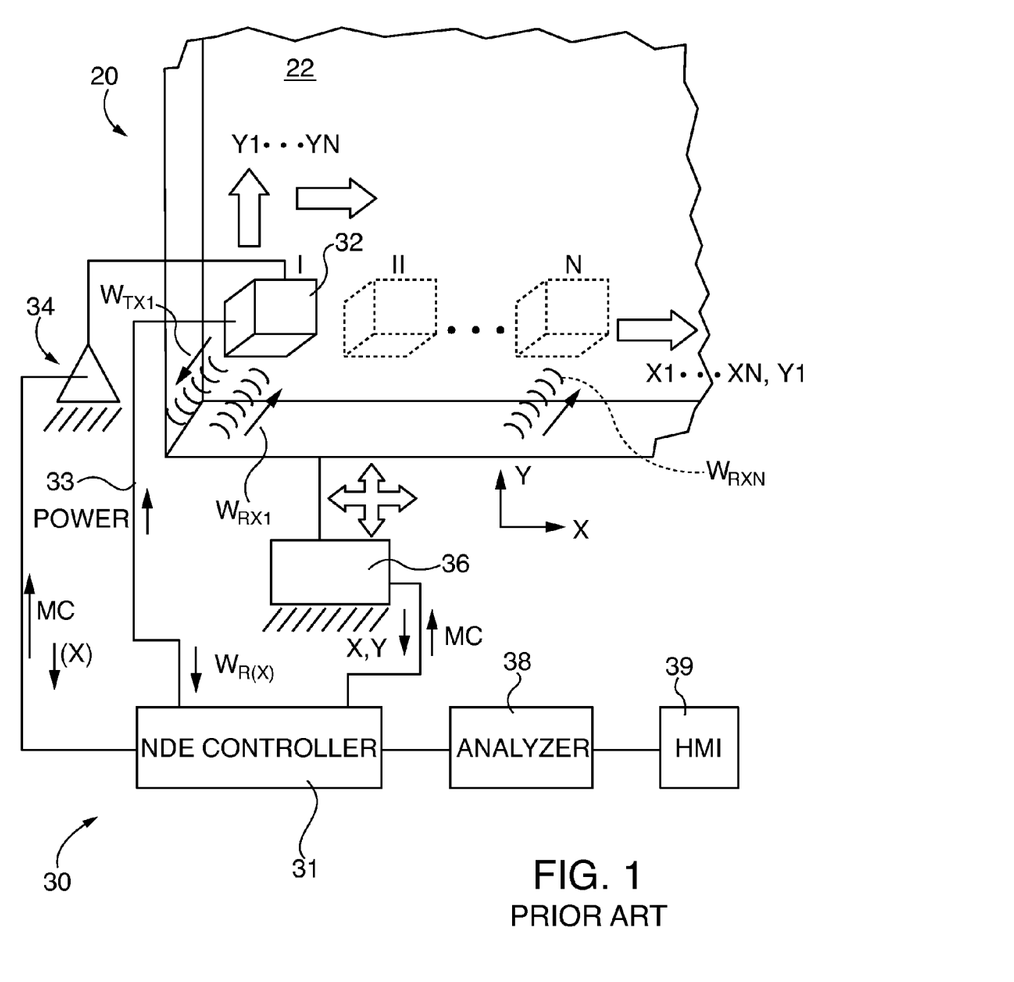
FIG. 1 is a schematic view of an embodiment of a known prior art nondestructive evaluation (NDE) scanning system employing motion-controlled positioning of the test probe that is translated along a single line axis.

Referring to FIG. 1, current technology for manual ultrasonic and eddy current inspection in industrial nondestructive testing modalities are limited to a single scanning axis, with the volume of test object sample or specimen 20 scanning limited by the probe's effective scan width along a scanned surface 22. Existing ultrasonic or eddy current NDE inspection test apparatuses 30 include an NDE controller 31 and a test probe 32 which are coupled by power and data cable 33. At a given test probe 32 spatial position on the surface 22 (e.g., position I) the probe transmits penetrating waves into the test sample top surface 22 and receives the reflected waveform data relevant to that spatial position. Using a test probe motion control system 34 and/or a test object motion control system 36 under general control by the NDE controller 31 (issuing motion control commands MC), the probe 32 is translated to other positions II-N along the X axis path, and waveform data are gathered for each of those positions. The motion control systems can be affixed to the probe or test sample so that all relative probe/test object positioning is controlled by those systems. Alternatively a free-hand probe that is not coupled to a probe motion control system can be moved along a controlled path across a test object by abutting the probe against a pre-positioned fixture of known coordinate location relative to the test object—analogous to abutting a pencil against a ruler to draw a straight line at a desired known position on a sheet of paper. Upon motion of the probe across the pre-defined translation path, a scan data set, matching spatial position data with the waveform data, are sent to the NDE analyzer 38 for transforming the scan data set into spatially mapped internal structural characterizations of the test object, e.g., voids, cracks, discontinuities, etc. The characterization information may be extracted for analysis via human machine interface (HMI) 39 or forwarded to other analysis or data storage devices for further processing.

Known NDE inspection systems 30 employ probe positioning motion control systems 34/36 with single wheel encoders and/or retractable line encoders, which are limited to single-dimensional line scans of test samples that correlate the motion control position across a line scanning path with waveform readings, such as the X axis path shown in FIG. 1. Due to the single-line scanning limitation, the scanner 30 evaluation of the test object 20 volume is limited to the probe 32 corresponding effective scanning width. When a larger volume of the test object 20 needs to be scanned the motion control system 34/36 follows a rastered path, which in the example of FIG. 1 moves the probe 32 and/or test object 20 to a different position on the motion control system 34 and/or 36 single wheel encoded orthogonal Y axis to complete another scan line across the X axis. As the motion control system 34/36 is incapable of free-hand multi-axis scanning, compliance with raster scan coordinate data gathering is required (i.e., some combination of controlled X and Y motions to gather accurate probe positional spatial data). Any deviation from the path predefined rastered pathways can lead to inaccurate correlation of scan data and spatial position. Also failure to follow organized rastered scanning protocols can lead to "gaps" in the acquired data scan sets, in which portions of the test object volume structure are not properly characterized.

While organized rastered scanning under motion control system positioning control facilitates NDE scanning of an entire test object volume, in some applications it may not be practical to transport a test object to an inspection site having a motion controlled NDE inspection system. Conversely, test object location or site limitations may also make it impractical to transport a motion-controlled NDE scanning system to the test object's field site.

Use of a full motion-controlled NDE scanning system may not be practical or convenient to conduct a limited local scan of only a portion of a test object in the field, where flexible or spontaneous use of a hand-held scanning probe system might be helpful for field service. Unfortunately, with present NDE scanning systems hand-held or free-hand scanning probe manipulation is not practical because spatial position and waveform data cannot be correlated accurately for NDE analyzer analysis of a test sample volume greater than an accessible at a single probe spatial position.

Thus, a need exists in the art for a waveform eddy current or ultrasound modality NDE system that can perform a multi-dimensional scan of a test object sample without use of a probe positioning motion control system, while maintaining NDE accuracy.

A need also exists in the art for a waveform eddy current or ultrasound modality NDE system that can perform a multi-dimensional scan of a test object sample with a hand-held scanning probe that is capable of selective free-hand, multi-dimensional spatial positioning by an operator, while maintaining NDE accuracy.

SUMMARY OF THE INVENTION

Accordingly, an object of the invention is to create a waveform eddy current or ultrasound modality NDE system that can perform a multi-dimensional scan of a test object sample without use of an expensive and complicated probe positioning motion control system, while maintaining NDE accuracy.

Another object of the invention is to create a waveform eddy current or ultrasound modality NDE system that can perform a multi-dimensional scan of a test object sample with a hand-held scanning probe that is capable of selective free-hand, multi-dimensional spatial positioning by an operator, while maintaining NDE accuracy, that is preferably easily transported and utilized on an impromptu basis at field locations.

These and other objects are achieved in accordance with the present invention by a scanning probe for an industrial nondestructive evaluation (NDE) ultrasound or eddy current scanning system. The scanning probe gathers reflected waveform data indicative of internal characteristics of the test object. The scanning probe also includes a self-contained multi-axis position encoder that correlates both multi-dimensional probe underside translation and rotation motion across the test sample surface with the multi-dimensional spatial location on the test object surface. The position encoder compensates for probe rotation that would otherwise negatively impact probe position determination accuracy. A data acquisition system combines sets of positional and waveform data for processing by an NDE analyzer.

Exemplary embodiments of the scanning probe multi-axis position encoder system employ opto-mechanical and opto-electrical encoders. An exemplary opto-mechanical encoder system implements a pair of parallel aligned orthogonal axis magnetic roller ball encoders that are of the type used in computer mouse human machine interface devices. The magnetic roller ball can be rubber coated for non-ferro magnetic substrates. An exemplary opto-electrical encoder implementation utilizes a pair of parallel aligned orthogonal axis laser tracking encoders that are of the type used in optical computer mice. Type of multi-axis encoder system can be either mounted directly to or incorporated within the ultrasonic or eddy current probe housing. The multi-axis encoders can transmit the encoder position data via a hardwired cable, wireless communication system or retain the positional data in probe onboard memory for subsequent downloading. The opto-mechanical roller ball device is desirable for ultrasonic inspection modalities, so that motion detection of the probe across the test surface will not be impaired by ultrasound wave couplant material that is often interposed between the test probe and the test object surface for ultrasound wave transmission quality. The electro-optical laser encoder system is suitable for eddy current applications where most parts are non-ferro magnetic and the inspection does not require a couplant intermediary between the probe and test object surface.

The present invention facilitates fast free-hand raster scans of test objects or free-hand unrestrained manipulation of the scanning probe without the need for motion control system scanning platforms. Thus the present invention scanning system can be easily transported and used at a field site to perform scans without the need to transport the test object or a motion control NDE scanner to other locations. NDE scans can now be performed on an impromptu basis at field sites by service technicians without the need to transport complicated motion control equipment, which may not be practical for use at the field site.

Embodiments of the present invention feature a reflected penetrating waveform scanning probe for nondestructive evaluation of a non-living test sample, including a housing having an underside for abutment against and multi-dimensional translation across a surface of a non-living test sample. Directed outwardly from the housing toward the surface are a test sensor system, and a probe position encoder system. The test sensor system is for transmitting a penetrating waveform into the test sample, receiving a reflected waveform from the test sample at a multi-dimensional spatial location on the test object surface and generating reflected waveform data corresponding to that location. The probe position encoder system correlates multi-dimensional probe underside translation and rotation motion across the test sample surface with the multi-dimensional spatial location on the test object surface, and generates corresponding multi-dimensional spatial location data. A scan data acquisition system is coupled to the test sensor and encoder systems, for receiving and correlating corresponding reflected waveform data at the location with its corresponding multi-dimensional spatial location data in a scan data set, and for sending the scan data set to a nondestructive evaluation analyzer.

Other embodiments of the present invention feature a reflected penetrating waveform scanning system for nondestructive evaluation of a non-living test sample, comprising a scanning probe, a scan data acquisition system and a nondestructive evaluation analyzer. The scanning probe has a housing with an underside for abutment against and multi-dimensional translation across a surface of a non-living test sample, and has directed outwardly toward the surface a test sensor system for transmitting a penetrating waveform into the test sample, receiving a reflected waveform from the test sample at a multi-dimensional spatial location on the test object surface and generating reflected waveform data corresponding to that location. The scanning probe housing also has directed outwardly toward the test surface a probe position encoder system that correlates multi-dimensional probe underside translation and rotation motion across the test sample surface with the multi-dimensional spatial location on the test object surface and that generates corresponding multi-dimensional spatial location data. The scan data acquisition system is coupled to the test sensor and encoder systems, for receiving and correlating corresponding reflected waveform data at the location with its corresponding multi-dimensional spatial location data in a scan data set, and for sending the scan data set to a nondestructive evaluation analyzer. The nondestructive evaluation analyzer is coupled to the scan data acquisition system, for receiving and transforming the scan data set into spatially mapped internal structural characterizations of the test object.

Additional embodiments of the present invention feature a method for nondestructive evaluation of a non-living test sample with a reflected penetrating waveform scanning system for nondestructive evaluation of a non-living test sample of the present invention. The NDE scanning system has a scanning probe, a scan data acquisition system and a nondestructive evaluation analyzer. The scanning probe has a housing with an underside for abutment against and multi-dimensional translation across a surface of a non-living test sample, and has directed outwardly toward the surface a test sensor system for transmitting a penetrating waveform into the test sample, receiving a reflected waveform from the test sample at a multi-dimensional spatial location on the test object surface and generating reflected waveform data corresponding to that location. The scanning probe housing also has directed outwardly toward the test surface a probe position encoder system that correlates multi-dimensional probe underside translation and rotation motion across the test sample surface with the multi-dimensional spatial location on the test object surface and that generates corresponding multi-dimensional spatial location data. The scan data acquisition system is coupled to the test sensor and encoder systems, for receiving and correlating corresponding reflected waveform data at the location with its corresponding multi-dimensional spatial location data in a scan data set, and for sending the scan data set to a nondestructive evaluation analyzer. The nondestructive evaluation analyzer is coupled to the scan data acquisition system, for receiving and transforming the scan data set into spatially mapped internal structural characterizations of the test object. The method is practiced by abutting the scanning probe underside against the test sample surface at a multi-dimensional spatial location and transmitting a penetrating waveform into the test sample. The reflected waveform is received from the test sample with the scanning probe and reflected waveform data corresponding to the location is generated. The scanning probe underside is translated and rotated across the test sample surface in multiple dimensions at a plurality of locations, while at each location generating reflected waveform data with the test sensor system and generating multi-dimensional spatial location data with the probe position encoder system. The scan data acquisition system receives and correlates the corresponding reflected waveform and multi-dimensional spatial location data at each of the plurality of locations into a scan data set. The scan data set is sent to the nondestructive evaluation analyzer, which transforms the scan data set into spatially mapped internal structural characterizations of the test object.

The objects and features of the present invention may be applied jointly or severally in any combination or sub-combination by those skilled in the art.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

After considering the following description, those skilled in the art will clearly realize that the teachings of the various embodiments of the present invention can be readily utilized in scanning probes for industrial nondestructive evaluation (NDE) ultrasound or eddy current scanning systems. The scanning probe gathers reflected waveform data indicative of internal characteristics of the test object. The scanning probe also includes a self-contained multi-axis position encoder that correlates both multi-dimensional probe underside translation and rotation motion across the test sample surface with the multi-dimensional spatial location on the test object surface. The position encoder compensates for probe rotation that would otherwise negatively impact probe position determination accuracy. A data acquisition system combines sets of positional and waveform data for processing by an NDE analyzer. Embodiments of the scanning system probes of the invention facilitate free-hand scanning procedures without the need for external motion control systems to orient the probe relative to the test object. Thus the scanning probes of the present invention can be hand-held units, which through the use of multi-axis translation and rotation position encoders accurately correlated multi-dimensional spatial position on the text object with scan waveform data acquired at that spatial position. The manual, hand-held multi-axis probe position encoder system that correlates multi-dimensional probe underside translation and rotation motion across the test sample surface with the multi-dimensional spatial location on the test object surface and that generates corresponding multi-dimensional spatial location data can be built, using a pair of known orthogonal position encoders that are often incorporated in computer mice, and aligning their corresponding orthogonal axes in parallel. In this manner when the probe is translated without rotation, both of the parallel axes encoder pairs will generate the same positional data. If the probe is rotated or twisted during its motion each of the encoders will generate different positional data. When the paired encoders generate different positional data the encoder system compensates for the twisting or rotational motion to generate multi-dimensional position data that accurately represents the probe position on the test object surface, or relative to the prior probe position.

As noted the multi-dimensional spatial location probe position encoder system can be built using existing sensor technology. One existing sensor option is a pair of magnetic roller balls (that could be rubber coated for scanning of non-ferro-magnetic substrates) with orthogonal, i.e., perpendicular optical encoding disks, such as those found in known roller ball computer mice. The roller ball mice embodiment is suitable for ultrasonic NDE applications, so that the motion detection will not be impaired by the couplant material that is typically interposed between the probe housing and the test surface. Alternatively, a pair of parallel oriented, orthogonal axis known CCD or CMOS optical positional sensors can be used, such as those utilized in a typical optical computer mouse. Opto-electronic position encoding sensors are suitable for use in eddy current NDE applications, where inspected parts are often constructed of non-ferro magnetic material and the inspection modality does not require a couplant material to be interposed between the scanning probe and the test surface.

NDE Scanning System Architecture

Figure 2:
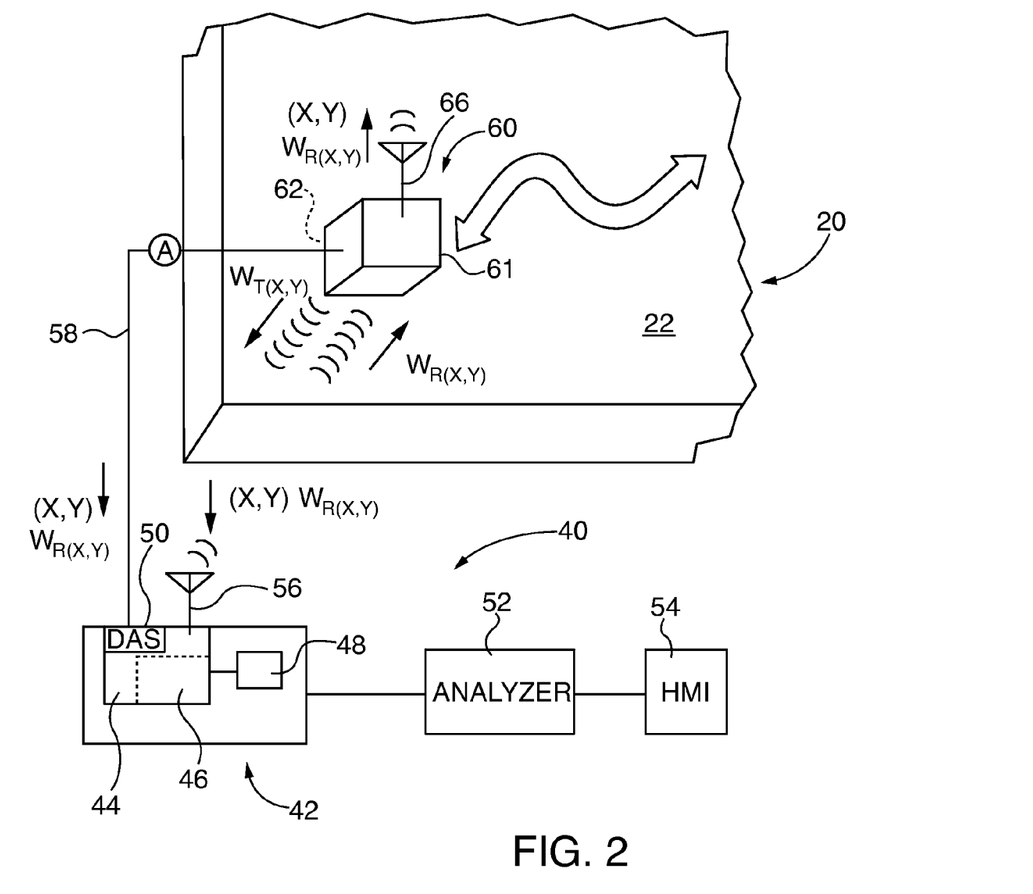
FIG. 2 is a schematic view of an embodiment of the nondestructive evaluation (NDE) scanning system of the present invention, employing a multi-dimensional axis probe position encoder system.
Figure 3:
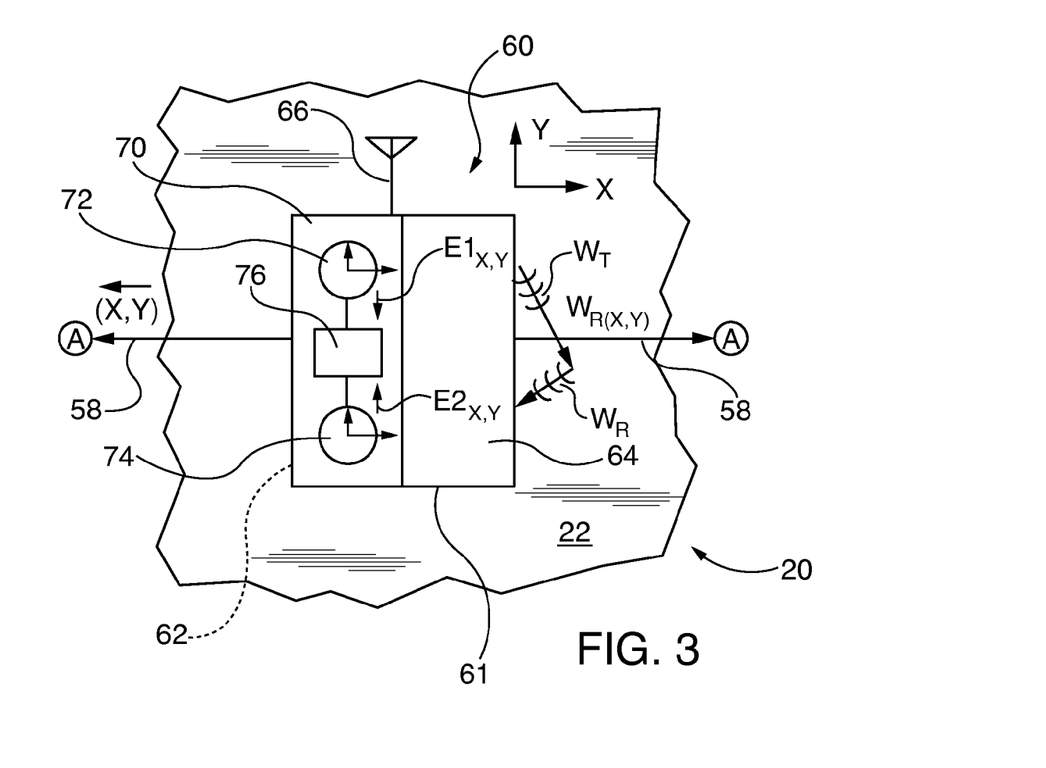
FIG. 3 is a combined schematic plan view and block diagram of an embodiment of the probe of the present invention, employing a pair of parallel-aligned orthogonal axis probe position encoders.

FIGS. 2 and 3 shows an exemplary embodiment of a test object 20 with a top scanned surface 22 that is being inspected by an NDE scanning system 40 of the present invention. The scanning system 40 has an NDE controller 42, which includes a processor 44 and known software instruction modules 46 stored in processor memory and/or memory 48. A data acquisition system (DAS) correlates acquired scanned waveform data sets with multi-axis spatial position on the test object surface 22. The DAS functions may be performed in the NDE controller processor 44, by executing software instructions 46 to perform the scan data and positional data correlation. The DAS combines the correlated waveform and positional data sets into a scan data set, for transfer to and analysis by the NDE analyzer 52. The NDE analyzer transforms the scan data set into spatially mapped internal structural characterizations of the test object, which may be evaluated on the human machine interface (HMI) 54 or passed to other data analysis and/or storage equipment.

The NDE controller 42 may establish external communication through wireless communication system 56 or a power/communications cable 58 to test probe 60 or other devices. The test probe 60 has a probe housing 61 and undersurface or underside 62 for abutment against and multi-dimensional translation/rotation across the surface 22 of the non-living test sample 20. The test probe 60 has a test sensor system 64 within or coupled to the housing 61, for transmitting a penetrating waveform $W_{T(X,Y)}$ into the test sample 20 and receiving a corresponding reflected waveform $W_{R(X,Y)}$ from the test sample at a multi-dimensional spatial location at a given coordinate position (X,Y) on the test object surface 22. The scanning probe housing 61 also has directed outwardly toward the test surface 22 a probe position encoder system 70 that correlates multi-dimensional probe underside translation and rotation motion across the test sample surface with the multi-dimensional spatial location on the test object surface and that generates corresponding multi-dimensional spatial location data. The position encoder system may be incorporated within or attached to the probe housing 61.

The scan data acquisition system (DAS) 50 is coupled to the test sensor 64 and encoder 70 systems, for receiving and correlating corresponding reflected waveform data at the location with its corresponding multi-dimensional spatial location data in a scan data set, and for sending the scan data set to a nondestructive evaluation analyzer 52. The nondestructive evaluation analyzer is coupled to the scan data acquisition system 50, for receiving and transforming the scan data set into spatially mapped internal structural characterizations of the test object. The scan data acquisition system 50 may be incorporated in the NDE controller 42 as a separate device or its functions may be incorporated within the controller. Alternatively the DAS 50 may be a separate component operatively coupled to the NDE controller 42 and scanning probe 60. In some embodiments the DAS may be affixed to or incorporated within the probe housing 61.

Figure 4:
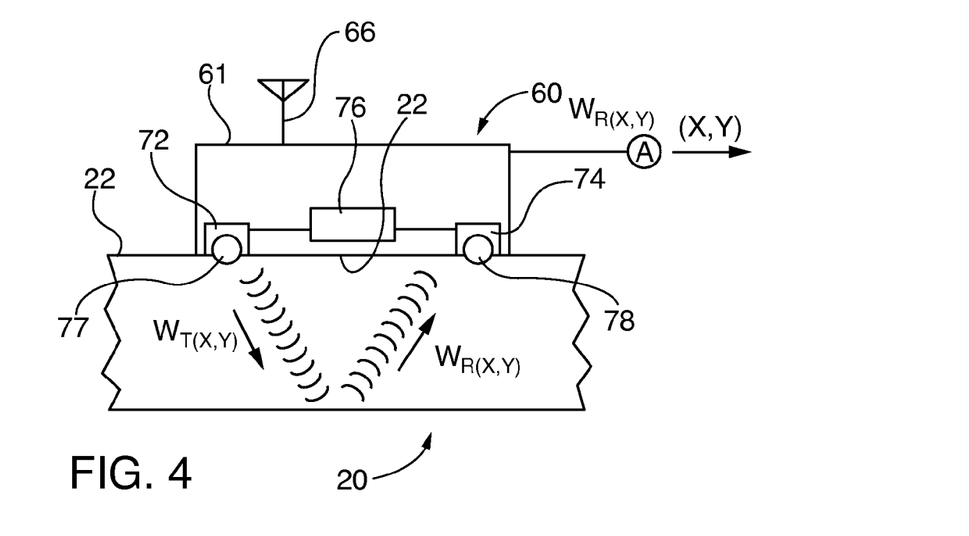
FIG. 4 is a combined schematic elevational view and block diagram of an embodiment of the probe of FIG. 3, employing a pair of parallel-aligned orthogonal axis opto-mechanical mouse ball encoders.
Figure 5:
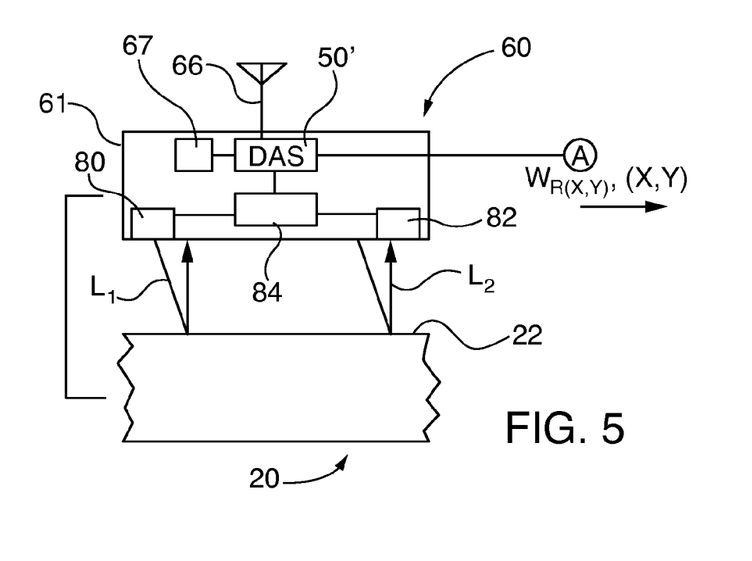
FIG. 5 is a combined schematic elevational view and block diagram of an embodiment of the probe of FIG. 3, employing a pair of parallel-aligned orthogonal axis electro-optical laser encoders.

Referring to FIGS. 3-5, the probe positioning encoder system 70 correlates multi-dimensional probe underside 61 translation and rotation motion across the test sample surface 22 with the multi-dimensional spatial location on the test object surface and that generates corresponding multi-dimensional spatial location data. In these embodiments, the positioning encoder system 70 has a paired set of parallel-aligned orthogonal axis first encoder 72 that generates a first encoder position signal $E1_{(X,Y)}$ and a second encoder 74 that generates a second encoder position signal $E2_{(X,Y)}$. As will be described in greater detail herein, the encoder system controller 76 converts, and if needed also compensates for rotational movement, the respective encoder 72, 74 position signals E1 and E2 into spatial location data X, Y.

In the embodiment of FIG. 4, the position encoders are first and second opto-mechanical sensors 77, 78 with mouse balls in contact with the test object surface 22. Probe 60 motion on the test object surface 22, which rotates the mouse balls 77, 78, is correlated with spatial position by the encoder system controller 76.

In the embodiment of FIG. 5, the position encoders are first and second opto-electronic encoders 80, 82, that respectively project and subsequently receive reflected photonic beams (often laser beams) L1 and L2 off the surface 22. Probe 60 motion on the test object surface 22, re-orients the reflected laser beams L1 and L2 on CCD or CMOS sensor arrays within the encoders 80, 82. The encoder output signals are correlated with spatial position by the encoder system controller 84. In the embodiment of FIG. 5 the DAS 50' is incorporated within the scanning probe housing 61. Correlated scan waveform and spatial position data sets are correlated in the DAS 50' and sent to the rest of the NDE system 40 by any chosen communication pathway, such as cable 58, wireless communication system 66 or stored in internal memory 67 within the probe 60 for subsequent downloading.

NDE Scanning System Architecture

Figure 6:
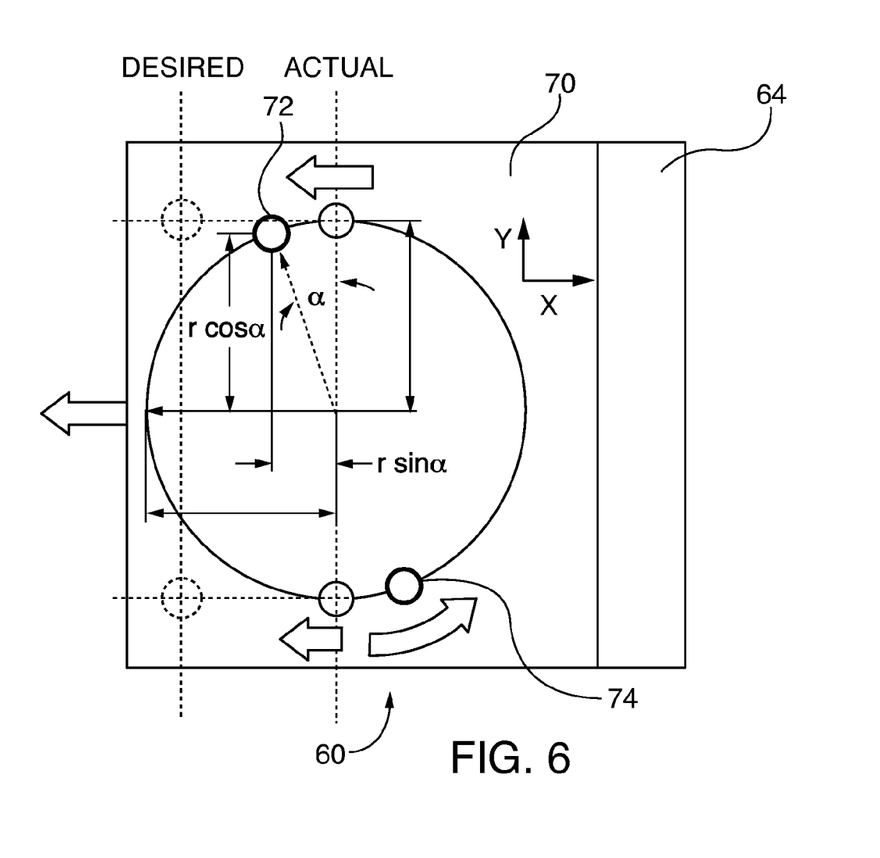
FIG. 6 is a plan schematic view of an embodiment the probe position encoder system of the present invention compensating for probe rotation through use of exemplary parallel-aligned orthogonal axis probe position encoders.
Figure 7:
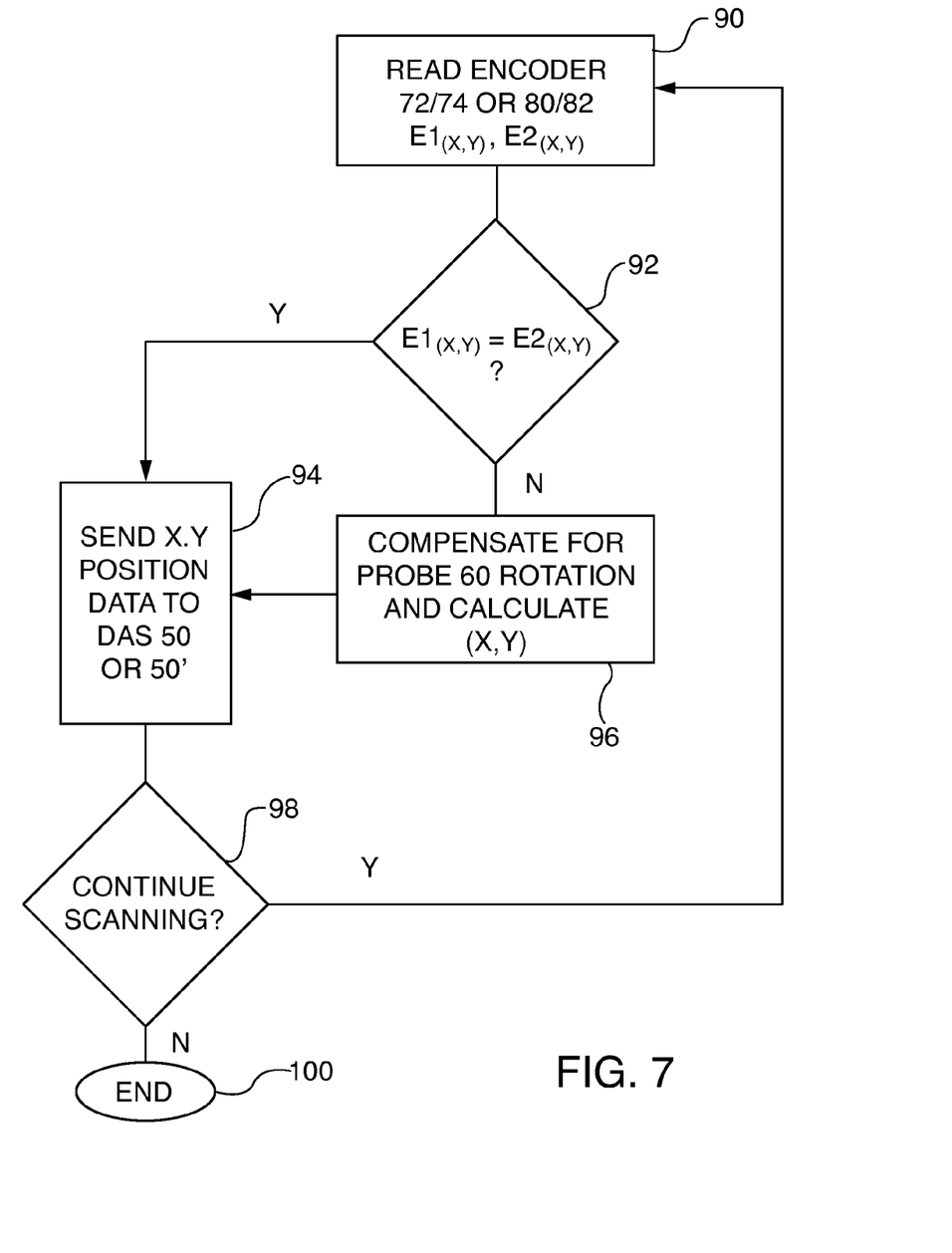
FIG. 7. is a plan flowchart of an embodiment of a method employed by the probe position encoder system of the present invention, to compensate for probe rotation by use of the parallel-aligned orthogonal axis probe position encoders.

Referring to FIGS. 6 and 7, the scanning probe 60 probe position encoder system 70 compensates for probe rotation/twisting during motion by comparing the respective position encoders 72, 74 parallel orthogonal axis outputs E1, E2 in the encoder system controller 76, DAS 50/50' or the NDE controller 42. In step 90 the respective encoder 72, 74 output readings E1(X,Y) and E2(X,Y) are read. In step 92 those readings are compared. If the output readings E1, E2 for both orthogonal axes are identical, no twist/rotation has occurred during probe 60 motion. Hence there is no reason to compensate for rotational movement and the X, Y position data are gathered by the DAS 50/50' for matching with waveform data $W_{R(X,Y)}$ for the corresponding position at step 94. Conversely, if the output readings E1, E2 are different, the encoder system compensates for the rotation at step 96 and routes the compensated position data (X,Y) to the DAS 50/50'. If the NDE scanning system is to continue scanning at step 98 more readings are read at step 90, with the sequential process 92-98 continuing until a cease scanning determination is made, at which time scanning ends at step 100.

An exemplary probe 60 rotation compensation correction is illustrated in FIG. 6, where the scanning probe 60 was intended to be translated horizontally to the left (−Y) direction of the figure in a straight line a distance r, with the motion reference point intended to be midway between the respective X positions of each sensor 72, 74 and along the common Y axis. If the intended translation was accomplished both the position encoders 72, 74 would have generated the same (X, Y) outputs (−r, 0). However, the inadvertent counter-clockwise rotation of α degrees has caused the encoders 72, 74 to be oriented in the bold highlighted actual positions. For generation of an accurate spatial position data set by the probe position encoder system 70 the encoder erroneous (X,Y) motion outputs must be corrected to reflect the probe rotation in the counterclockwise α angular position. If, as shown in FIG. 6, the probe 60 and its probe position encoder system 70 are unintentionally rotated by an angle α, the unintended starting locations of the two sensors 72, 74 will be indicated by the bold circles rather than the intended motion lighter circles. Once the encoder system is rotated counter clockwise α degrees before intended translation, when it is moved in the −x direction by a distance r, a compensated encoder X axis position of $-r*\sin(\alpha)$ will be sent to the DAS 50/50', instead of erroneous −r position reading. Similarly the corrected Y direction of travel of $-r*\cos(\alpha)$ will be sent to the DAS 50/50' rather than zero.

Figure 8:
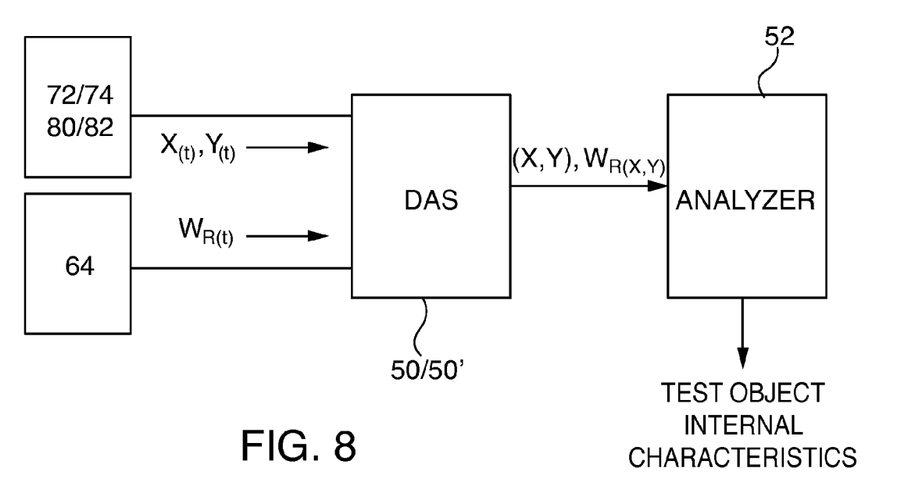
FIG. 8 is a block diagram of an embodiment of an embodiment of a scan data acquisition system of the present invention, for correlating corresponding reflected waveform data gathered by the sensor system with corresponding multi-dimensional spatial location data, using time domain sampling techniques.
Figure 9:
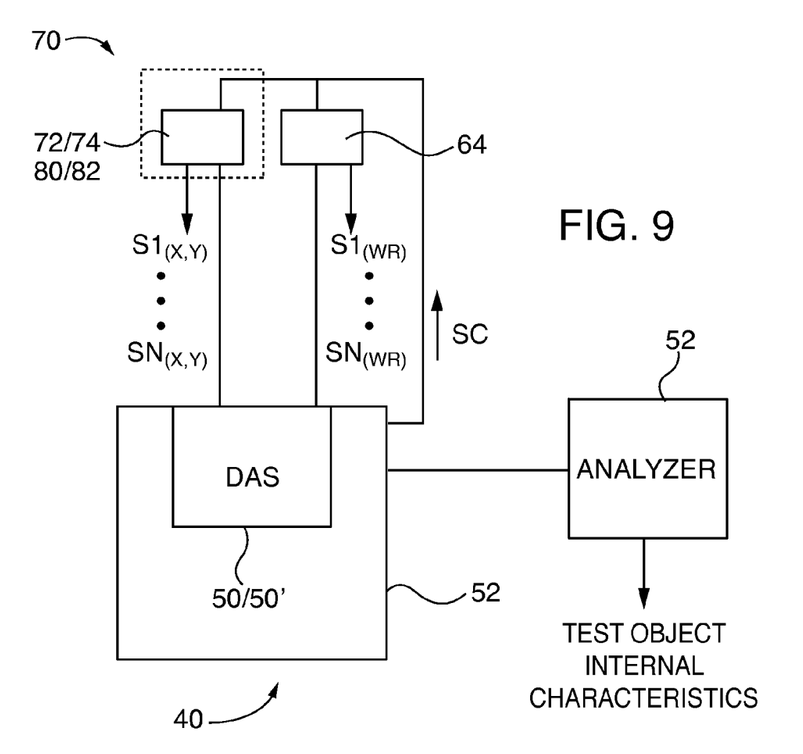
FIG. 9 is a block diagram of an embodiment of an embodiment of a scan data acquisition system of the present invention, for correlating corresponding reflected waveform data gathered by the sensor system with corresponding multi-dimensional spatial location data, using synchronized data sampling techniques.

The data acquisition system 50/50' correlates reflected waveform data $W_R$ and multi-dimensional spatial location data (X,Y) in a scan data set containing corresponding spatial position and waveform data for analysis by the NDE analyzer 52. In FIG. 8 scan waveform $W_R(t)$ and spatial position data (X,Y)(t) matched temporally by assigning time stamps to samples, with the DAS matching identical or nearly identical time stamps to create the scan data set (X,Y), $W_{R(X,Y)}$. In FIG. 9 the DAS 50/50' and/or the NDE controller 52 are coupled to and issue sample commands to the respective scan test sensor system 64 and the probe position encoder system 70 so that sampling by both systems, S1(X,Y)-SN(X,Y) and S1($W_R$)-SN($W_R$) is synchronized in parallel (by issuance of a sample command SC) to create the composite scan data set to the analyzer 52. Other known data matching methods for creating a composite matched data set of waveform data and positional data may be substituted for the exemplary matching methods described in these embodiments.

Composite scan data sets of waveform data and positional data, no matter how gathered or compiled, are then utilized by a known ultrasound, eddy current or other reflected waveform modality NDE analyzer 52, where they are transformed into spatially mapped internal structural characterizations of the test object using known techniques.

Although various embodiments that incorporate the teachings of the present invention have been shown and described in detail herein, those skilled in the art can readily devise many other varied embodiments that still incorporate these teachings. The invention is not limited in its application to the exemplary embodiment details of construction and the arrangement of components set forth in the description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional hems. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

What is claimed is:

1. A reflected penetrating waveform scanning probe for nondestructive evaluation of a non-living test sample, comprising:

a housing having an underside for abutment against and multi-dimensional translation across a surface of a non-living test sample, and having directed outwardly toward the surface:

a test sensor system for transmitting a penetrating waveform into the test sample, receiving a reflected waveform from the test sample at a multi-dimensional spatial location on the test sample surface and generating reflected waveform data corresponding to that location; and a probe position encoder system that correlates multi-dimensional probe underside translation and rotation motion across the test sample surface with the multi-dimensional spatial location on the test sample surface and that generates corresponding multi-dimensional spatial location data, said probe position encoder system having a pair of first and second orthogonal axes position encoders respectively generating first and second orthogonal axes position readings, with the respective corresponding orthogonal axes in mutual parallel alignment, said probe position encoder system compensating for probe rotation when the respective first and second orthogonal axes position readings differ, while generating said multi-dimensional spatial location data; and a scan data acquisition system, coupled to the test sensor and encoder systems, for receiving and correlating corresponding reflected waveform data at the location with its corresponding multi-dimensional spatial location data in a scan data set, and for sending the scan data set to a nondestructive evaluation analyzer.

2. The scanning probe of claim 1, the first and second orthogonal axes position encoders comprising a pair of opto-mechanical mouse balls in contact with the test sample surface.

3. The scanning probe of claim 1, the first and second orthogonal axes position encoders comprising a pair of opto-electronic mice sensors that project photonic beams on the test sample surface.

4. The scanning probe of claim 1, the test sensor system comprising an ultrasound transmitter and receiver.

5. The scanning probe of claim 1, the test sensor system comprising an eddy current transmitter and receiver.

6. The scanning probe of claim 1, the reflected waveform data and the multi-dimensional spatial location data including time stamps when these data were generated; and the scan data acquisition system matching time stamps to correlate corresponding waveform and location data.

7. The scanning probe of claim 1, the scan data acquisition system correlating respective waveform data and the multi-dimensional spatial location data by synchronizing their generation or capture.

8. A reflected penetrating waveform scanning system for nondestructive evaluation of a non-living test sample, comprising:
a scanning probe having a housing with an underside for abutment against and multi-dimensional translation across a surface of a non-living test sample, and having directed outwardly toward the surface:
a test sensor system for transmitting a penetrating waveform into the test sample, receiving a reflected waveform from the test sample at a multi-dimensional spatial location on the test sample surface and generating reflected waveform data corresponding to that location; and
a probe position encoder system that correlates multi-dimensional probe underside translation and rotation motion across the test sample surface with the multi-dimensional spatial location on the test sample surface and that generates corresponding multi-dimensional spatial location data, said probe position encoder system having a pair of first and second orthogonal axes position encoders respectively generating first and second orthogonal axes position readings, with the respective corresponding orthogonal axes in mutual parallel alignment, said probe position encoder system compensating for probe rotation when the respective first and second orthogonal axes position readings differ, while generating said multi-dimensional spatial location data;
a scan data acquisition system, coupled to the test sensor and encoder systems, for receiving and correlating corresponding reflected waveform data at the location with its corresponding multi-dimensional spatial location data in a scan data set, and for sending the scan data set to a nondestructive evaluation analyzer; and
a nondestructive evaluation analyzer coupled to the scan data acquisition system, for receiving and transforming the scan data set into spatially mapped internal structural characterizations of the test object.

9. The scanning system of claim 8, the first and second orthogonal axes position encoders comprising a pair of opto-mechanical mouse balls in contact with the test sample surface.

10. The scanning system of claim 8, the first and second orthogonal axes position encoders comprising a pair of opto-electronic mice sensors that project photonic beams on the test sample surface.

11. The scanning system of claim 8, the test sensor system comprising an ultrasound transmitter and receiver.

12. The scanning system of claim 8, the test sensor system comprising an eddy current transmitter and receiver.

13. The scanning system of claim 8, the scan data acquisition system correlating respective waveform data and the multi-dimensional spatial location data by:
synchronizing their generation or capture; or
time stamping and matching time stamps of the respective waveform data and the multi-dimensional spatial location data.

14. A method for nondestructive evaluation of a non-living test sample, comprising:
providing a reflected penetrating waveform scanning system for nondestructive evaluation of a non-living test sample, having:
a scanning probe having a housing with an underside for abutment against and multi-dimensional translation across a surface of a non-living test sample, and having directed outwardly toward the surface, said scanning probe including:
a test sensor system for transmitting a penetrating waveform into the test sample, receiving a reflected waveform from the test sample at a multi-dimensional spatial location on the test sample surface and generating reflected waveform data corresponding to that location; and
a probe position encoder system that correlates multi-dimensional probe underside translation and rotation motion across the test sample surface with the multi-dimensional spatial location on the test sample surface and that generates corresponding multi-dimensional spatial location data, said probe position encoder system having a pair of first and second orthogonal axes position encoders respectively generating first and second orthogonal axes position readings, with the respective corresponding orthogonal axes in mutual parallel alignment, said probe position encoder system compensating for probe rotation when the respective first and second orthogonal axes position readings differ, while generating said multi-dimensional spatial location data;
a scan data acquisition system, coupled to the test sensor and encoder systems, for receiving and correlating corresponding reflected waveform data at the location with its corresponding multi-dimensional spatial location data in a scan data set; and
a nondestructive evaluation analyzer coupled to the scan data acquisition system, for receiving and transforming the scan data set into spatially mapped internal structural characterizations of the test object;
abutting the scanning probe underside against the test sample surface at a multi-dimensional spatial location and transmitting a penetrating waveform into the test sample;

receiving the reflected waveform from the test sample with scanning probe and generating reflected waveform data corresponding to the location;

translating and rotating the scanning probe underside across the test sample surface in multiple dimensions at a plurality of locations, while at each location generating reflected waveform data with the test sensor system and generating multi-dimensional spatial location data with the probe position encoder system, said probe position encoder system compensating for probe rotation by determining whether the respective pairs of axes have the same position reading and compensating for rotation when the respective pairs have different position readings;

receiving and correlating the corresponding reflected waveform and multi-dimensional spatial location data at each of the plurality of locations into a scan data set with the scan data acquisition system; and sending the scan data set to the nondestructive evaluation analyzer and transforming the scan data set into spatially mapped internal structural characterizations of the test object.

15. The method of claim 14, the compensation rotation comprising multiplying the readings by sine or cosine of the rotation angle to obtain the actual probe location.

16. The method of claim 14, the first and second orthogonal axes position encoders comprising a pair of opto-mechanical mouse balls in contact with the test sample surface or a pair of opto-electronic mice sensors that project photonic beams on the test sample surface.

17. The method of claim 14, further comprising correlating respective waveform data and the multi-dimensional spatial location data by:
synchronizing their generation or capture; or
time stamping and matching time stamps of the respective waveform data and the multi-dimensional spatial location data.

* * * * *